United States Patent
Cook et al.

(10) Patent No.: US 12,365,948 B2
(45) Date of Patent: *Jul. 22, 2025

(54) DIAGNOSTIC TEST FOR PREDICTING METASTASIS AND RECURRENCE IN CUTANEOUS MELANOMA

(71) Applicant: Castle Biosciences, Inc., Friendswood, TX (US)

(72) Inventors: Robert Willis Cook, Houston, TX (US); Derek Maetzold, Friendswood, TX (US); Kristen Oeschlager, Phoenix, AZ (US)

(73) Assignee: CASTLE BIOSCIENCES, INC., Friendswood, TX (US)

( * ) Notice: Subject to any disclaimer, the term of this patent is extended or adjusted under 35 U.S.C. 154(b) by 252 days.

This patent is subject to a terminal disclaimer.

(21) Appl. No.: 17/883,223

(22) Filed: Aug. 8, 2022

(65) Prior Publication Data

US 2023/0077559 A1    Mar. 16, 2023

Related U.S. Application Data

(63) Continuation of application No. 16/745,998, filed on Jan. 17, 2020, now Pat. No. 11,434,536, which is a continuation of application No. 15/075,133, filed on Mar. 19, 2016, now Pat. No. 10,577,660, which is a continuation of application No. 14/193,378, filed on Feb. 28, 2014, now abandoned.

(60) Provisional application No. 61/783,755, filed on Mar. 14, 2013.

(51) Int. Cl.
C12Q 1/68 (2018.01)
C12Q 1/6886 (2018.01)

(52) U.S. Cl.
CPC ...... *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,642,279 | B2 | 2/2014 | Harbour |
| 8,822,149 | B2 | 9/2014 | Black et al. |
| 10,577,660 | B2 | 3/2020 | Cook et al. |
| 2007/0082347 | A1 | 4/2007 | Lanchbury et al. |
| 2008/0113360 | A1 | 5/2008 | Riker et al. |
| 2011/0123997 | A1 | 5/2011 | Kashani-Sabet et al. |
| 2011/0124525 | A1 | 5/2011 | Harbour |
| 2011/0159496 | A1 | 6/2011 | Kashani-Sabet et al. |
| 2011/0182881 | A1 | 7/2011 | Chin et al. |

FOREIGN PATENT DOCUMENTS

| | | |
|---|---|---|
| WO | 2006/092610 | 9/2006 |
| WO | 2009/131733 | 10/2009 |
| WO | 2009/132126 | 10/2009 |
| WO | 2011/039734 | 4/2011 |
| WO | 2012/040168 | 3/2012 |
| WO | 2012/125411 | 9/2012 |

OTHER PUBLICATIONS

Slonin, Nature Genetics Supplement, vol. 32, Dec. 2002, pp. 502-508.*
Michiels et al. Lancet, 2005; 365:488-492.*
Cheung et al (Nature Genetics, vol. 33, pp. 422-425; (2003)).*
Bittner et al., "Molecular classification of cutaneous malignant melanoma by gene expression profiling." Nature 406:536-40 (2000).
Brem et al., "Identification of Metastasis-Associated Genes by Transcriptional Profiling of a Metastasizing Versus a Non-Metastasizing Human Melanoma Cell Line" Anticancer Research 21(3B):1731-40 (2001).
Brunner et al., "A nine-gene signature predicting clinical outcome in cutaneous melanoma." J Cancer Res Clin Oncol. 139(2):249-58 (2013).
Haqq et al., "The gene expression signatures of melanoma progression" PNAS USA 102(17):6092-97 (2005).
Harbst et al., "Molecular profiling reveals low- and high-grade forms of primary melanoma." 18(15):4026-36 (2012).
Hoek et al., "Metastatic potential of melanomas defined by specific gene expression profiles with no BRAF signature." Pigment Cell Res. 19(4):290-302 (2006).
Huang et al., "LC/MS-Based Quantitative Proteomic Analysis of Paraffin-Embedded Archival Melanomas Reveals Potential Proteomic Biomarkers Associated with Metastasis" PLOS ONE 4(2): e4430 (pp. 1-12) (2009).
Jaeger et al., "Gene Expression Signatures for Tumor Progression, Tumor Subtype, and Tumor Thickness in Laser-Microdissected Melanoma Tissues" Clinical Cancer Research 13(3):806-15 (2007).
Kashani-Sabet. "Molecular markers in melanoma." Br J Dermatol. 170(1):31-35 (Jan. 2014).
Kashani-Sabet et al., "A multimarker prognostic assay for primary cutaneous melanoma." Clin Cancer Res. 15(22):6987-92 (2009).
Koh et al., "Differential gene expression profiling of primary cutaneous melanoma and sentinel lymph node metastases." Mod Pathol. 25(6):828-37 (2012).

(Continued)

*Primary Examiner* — Jehanne S Sitton
(74) *Attorney, Agent, or Firm* — McDonnell Boehnen Hulbert & Berghoff LLP

(57) ABSTRACT

The invention as disclosed herein in encompasses a method for predicting the risk of metastasis of a primary cutaneous melanoma tumor, the method encompassing measuring the gene-expression levels of at least eight genes selected from a specific gene set in a sample taken from the primary cutaneous melanoma tumor; determining a gene-expression profile signature from the gene expression levels of the at least eight genes; comparing the gene-expression profile to the gene-expression profile of a predictive training set; and providing an indication as to whether the primary cutaneous melanoma tumor is a certain class of metastasis or treatment risk when the gene expression profile indicates that expression levels of at least eight genes are altered in a predictive manner as compared to the gene expression profile of the predictive training set.

7 Claims, 7 Drawing Sheets

(56) References Cited

OTHER PUBLICATIONS

Ma et al., "Measurements of tumor cell autophagy predict invasiveness, resistance to chemotherapy, and survival in melanoma." Clin Cancer Res. 17(10):3478-89 (May 2011; Epub Feb. 15, 2011).
Mandala and Massi. "Tissue prognostic biomarkers in primary cutaneous melanoma." Virchows Arch. 464(3):265-81 (Mar. 2014; Epub Feb. 1, 2014).
Mauerer et al., "Identification of new genes associated with melanoma" Experimental Dermatology 20(6):502-07 (2011).
Onken et al., "Gene expression profiling in uveal melanoma reveals two molecular classes and predicts metastatic death." Cancer Res. 64:7205-9 (2004).
Onken et al., "An accurate, clinically feasible multi-gene expression assay for predicting metastasis in uveal melanoma." J Mol Diagn. 12:461-68 (2010).
Roberts et al., "Identification of methods for use of formalin-fixed, paraffin-embedded tissue samples in RNA expression profiling." Genomics. 94(5):341-48 (Nov. 2009; Epub Aug. 4, 2009).
Scatolini et al., "Altered molecular pathways in melanocytic lesions." Int J Cancer 126:1869-81 (2010).
Smith et al., "Whole-genome expression profiling of the melanoma progression pathway reveals marked molecular differences between nevi/melanoma in situ and advanced-stage melanomas." Cancer Biol Ther. 4:1018-29 (2005).
Swoboda et al., "Identification of genetic disparity between primary and metastatic melanoma in human patients." Genes Chromosomes Cancer 50(9):680-88 (2011).
Torabian and Kashani-Sabet, "Biomarkers for melanoma." Curr Opin Oncol. Review 17(2):167-71 (Mar. 2005).
Winnepenninckx et al., "Gene expression profiling of primary cutaneous melanoma and clinical outcome." J Natl Cancer Inst. 98:472-82 (2006).
Xu et al., "Gene expression changes in an animal melanoma model correlate with aggressiveness of human melanoma metastases." Mol Cancer Res. 6(5):760-69 (May 2008).
Xu et al., "Gene expression changes in an animal melanoma model correlate with aggressiveness of human melanoma metastases." Mol Cancer Res. 6(5):760-69 (May 2008).—Supplementary Table S3.
Xu et al., "Differential expression of microRNAs during melanoma progression: miR-200c, miR-205 and miR-211 are downregulated in melanoma and act as tumour suppressors" British Journal of Cancer 106(3):553-61 (2012).
Invitation to pay additional fees for International Application No. PCT/US2014/019326; mailed Jun. 25, 2014, pp. 1-12.
International Search Report and Written Opinion of the International Search Authority for International Application No. PCT/US2014/019326; mailed Aug. 26, 2014, pp. 1-18.
Harbour et al., "Frequent Mutation of BAP1 in Metastasizing Uveal Melanomas" Science 330(6009):1410-13 (Dec. 2010).
Rambaldi et al., "Splicy: a web-based tool for the prediction of possible alternative splicing events from Affymetrix probeset data" BMC Bioinformatics 8(Suppl I):S17 pp. 1-8 (Mar. 2007).
Schadendorf et al., "Advances and perspectives in immunotherapy of melanoma" Annals of Oncology 23(Supplement 10):x104-x108 (Sep. 2012).
Valsecchi et al., "Lymphatic Mapping and Sentinal Lymph Node Biopsy in Patients with Melanoma: A Meta-Analysis" Journal of Clinical Oncology 29(11):1479-1487 (Apr. 2011).
Garbe et al., "Systematic Review of Medical Treatment in Melanoma: Current Status and Future Prospects", The Oncologist, 16(1):5-24 (Jan. 2011).

\* cited by examiner

DIAGNOSTIC TEST FOR PREDICTING METASTASIS AND RECURRENCE IN CUTANEOUS MELANOMA

CROSS-REFERENCE TO RELATED APPLICATIONS

This application is a continuation of U.S. application Ser. No. 16/745,998, Jan. 17, 2020, which is a continuation of U.S. application Ser. No. 15/075,133, filed Mar. 19, 2016 (now U.S. Pat. No. 10,577,660; issued Mar. 3, 2020), which is a continuation of U.S. application Ser. No. 14/193,378, filed Feb. 28, 2014, and which claims the benefit of U.S. Provisional Application No. 61/783,755, filed Mar. 14, 2013, the disclosures of each of which are explicitly incorporated by reference herein in their entirety.

BACKGROUND OF THE INVENTION

Cutaneous melanoma (CM) is an aggressive form of cancer presenting over 76,000 diagnosed cases in 2012.[1] CM tumors develop through a number of discreet stages during the progression from a benign melanocytic nevus to a malignant metastatic tumor. Generally, benign nevi present as thin, pigmented lesions. After the acquisition of key genetic mutations and the initiation of cytoarchitectural modifications leading to shallow invasion of the skin, the lesions begin growing radially, a process referred to as the radial growth phase. Upon escape from growth control mediated by surrounding keratinocytes, stromal invasion to deeper regions of the dermis occurs, marking the progression to the vertical growth phase. The vertical growth phase, along with the genetic alterations that accompany this process, is thought to be the critical stepping stone in the development of metastatic melanoma.

As is common in many other cancers, if CM is detected in the early stages of tumor progression and appropriately treated, then a long-term metastasis free and overall survival following diagnosis is likely for the majority of patients.[2,3] For example, subjects diagnosed with low risk, stage I CM tumors have a 5-year overall survival rate of 91-97%.[3] A number of histological factors are used to stage CM and are associated with prognosis. These factors include Breslow thickness, mitotic index, ulceration, and spread of disease from the primary tumor to sentinel and/or regional lymph nodes.[3-7] Tumor stage is determined based upon these histopathological parameters using the well-known TNM (T=primary tumor, N=regional lymph nodes, M=distant metastases) system that defines stages 0-IV.[3] The TNM staging system is highly accurate for metastasis-free survival for stage 0 melanomas (5-year survival of 99%), and stage IV melanomas (5-year survival <10%), in which distant metastasis was detected at the time of primary diagnosis. Metastasis and short-term survival has been documented for subjects with stage I disease, with 5-10% of stage I tumors reporting metastatic activity. So, while the majority of patients with clinical stage I disease have a low chance of metastasis risk disease some patients will develop metastatic disease.

Prognosis for clinical stage II and stage III cases has poor accuracy as there is a large range within each stage and a larger overlap between the stages in 5-year survival rates. Under the current staging system, the 5-year survival rate for clinical stage II subjects is 53-82%, while the stage III 5-year survival is rate 22-68%.[3,8] The distinguishing hallmark between clinical stage II and stage III tumors is the presence of localized metastasis of CM cells in the sentinel lymph node (SLN). Patients with a positive SLN are clinical stage III. However, high false negative rates and disease recurrence are associated with histological analysis of SLNs as evidenced by the wide ranges of metastatic free survival and overall survival in stage II and III patients. Immunohistochemical and genetic amplification techniques designed to improve the common hematoxylin and eosin staining methods for detection of regional disease have been developed but only provide marginal improvements[9,10]. Biomarkers have been identified in SLN tissue, and analyzed to improve the ability to recognize CM cells in SLNs, however, these methods have limited improvement in accuracy and are compounded by extensive tissue sampling from invasive biopsy of the lymph node.[6,11] In addition, melanomas can enter the blood directly by intravasating into venous capillaries. Thus, the low sensitivity of SLN biopsy may relate to a direct hematogenous metastatic event versus an inaccurate SLN biopsy result.

Inaccurate prognosis for metastatic risk has profound effects upon patients that are treated according to a population approach rather than an individual or personalized approach. For example, CM patients categorized as stage III through the use of current histological techniques, but who have an actual individual risk of metastasis that is low (false positive), are inappropriately exposed to over-treatment that includes enhanced surveillance, nodal surgery, and chemotherapy.[12] Similarly, patients determined to have stage I or II disease who actually have a high risk for metastasis (false negative), are at risk of under-treatment. In addition, SLN biopsy exposes patients to significant clinical complications, such as lymphedema, and has a low positivity rate. For example, guidelines currently recommend that patients with CM staged at 1b (Breslow's thickness ≥0.75 mm but <1.00 mm or presence of ≥1 mitosis at any Breslow's thickness) are recommended to undergo SLN biopsy yet only 5% of SLN yield positivity. Meaning that of 20 patients with stage 1b melanomas who undergo SLN biopsy, 19 will be negative and exposed to a surgical complication of SLN biopsy.[12] Similarly, all pathologic stage II patients (Breslow's thickness >1.0 mm are recommended to undergo SLN biopsy yet only 18% will have a positive SLN.[12,13]

To this end, gene expression profile (GEP) signatures have been developed and some have been shown to have powerful prognostic capabilities in a number of malignant diseases[14-18]. One such signature has been used for prognostication of uveal melanoma, a tumor of melanocytic origin that develops in the eye. Like cutaneous melanoma, treatment of the primary uveal tumor is highly effective. 2-4% of uveal melanoma patients present with evidence of clinical metastasis at the time of diagnosis, yet up to 50% of uveal melanoma patients develop systemic metastases within five years of diagnosis regardless of primary eye tumor treatment (radiation therapy or enucleation)[19]. This means that a micrometastatic event has occurred in approximately 50% of uveal melanoma patients prior to primary eye tumor treatment. A GEP signature has recently been developed that can accurately distinguish uveal melanoma tumors that have a low risk of metastasis from those that have a high risk[14,20]. To assess genetic expression RT-PCR analysis is performed for fifteen genes (twelve discriminating genes and three control genes) that are differentially expressed in tumors with known metastatic activity compared to tumors with no evidence of metastasis. The uveal melanoma gene signature separates cases into a low risk group that has greater than 95% metastasis free survival five years after diagnosis, and a high risk group with less than 20% metastasis free survival at the same time point. The signature has been extensively validated in the clinical setting, and has been shown to provide a significant improvement in prognostic accuracy compared to classification by TNM staging criteria[20,21].

A number of groups have published genomic analysis of tumors in cutaneous melanoma[22-29]. While some studies have focused on the genetic alterations in malignant melanoma cells compared to normal melanocytes, others have compared benign nevi to tumors in the radial or vertical growth phases, or primary tumor to metastatic tumors. At the time the studies contained within this patent were designed and implemented (2010), no evidence could be found in the literature or other public domain sources that indicated a gene expression profile test focused solely on the primary melanoma tumor could be developed for the clinical application of predicting metastasis in patients with CM.[22-24,27-29] In addition, all studies utilized fresh frozen CM samples rather than formalin fixed paraffin embedded (FFPE) tumor tissue. All of the studies related to this invention have only used FFPE primary tumor tissue.

SUMMARY OF THE INVENTION

There is a need in the art for a more objective method of predicting which tumors display aggressive metastatic activity. Development of an accurate molecular footprint, such as the gene expression profile assay encompassed by the invention disclosed herein, by which CM metastatic risk could be assessed from primary tumor tissue would be a significant advance forward for the field.

In one embodiment, the invention as disclosed herein is a method for predicting the risk of metastasis of a primary cutaneous melanoma tumor, the method comprising: (a) measuring the gene-expression levels of at least eight genes selected from the group consisting of BAP1_varA, BAP1_varB, MGP, SPP1, CXCL14, CLCA2, S100A8, BTG1, SAP130, ARG1, KRT6B, GJA, ID2, EIF1B, S100A9, CRABP2, KRT14, ROBO1, RBM23, TACSTD2, DSC1, SPRR1B, TRIM29, AQP3, TYRP1, PPL, LTA4H, and CST6, in a sample taken from the primary cutaneous melanoma tumor, wherein measuring gene-expression levels of the at least eight genes comprises measurement of a level of fluorescence by a sequence detection system following RT-PCR; (b) determining a gene-expression profile signature comprising the gene expression levels of the at least eight genes; (c) comparing the gene-expression profile to the gene-expression profile of a predictive training set; and (d) providing an indication as to whether the primary cutaneous melanoma tumor is class 1 or class 2 of metastasis when the gene expression profile indicates that expression levels of at least eight genes are altered in a predictive manner as compared to the gene expression profile of the predictive training set.

In another embodiment, the invention as disclosed herein is a method for predicting the risk of metastasis of a primary cutaneous melanoma tumor, the method comprising: (a) measuring the gene-expression levels of at least eight genes selected from the group consisting of BAP1_varA, BAP1_varB, MGP, SPP1, CXCL14, CLCA2, S100A8, BTG1, SAP130, ARG1, KRT6B, GJA, ID2, EIF1B, S100A9, CRABP2, KRT14, ROBO1, RBM23, TACSTD2, DSC1, SPRR1B, TRIM29, AQP3, TYRP1, PPL, LTA4H, and CST6, in a sample taken from the primary cutaneous melanoma tumor, wherein measuring gene-expression levels of the at least eight genes comprises measurement of a level of fluorescence by a sequence detection system following RT-PCR; (b) determining a gene-expression profile signature comprising the gene expression levels of the at least eight genes; (c) comparing the gene-expression profile to the gene-expression profile of a predictive training set; and (d) providing an indication as to whether the primary cutaneous melanoma tumor is class A, class B, or class C of metastasis when the gene expression profile indicates that expression levels of at least eight genes are altered in a predictive manner as compared to the gene expression profile of the predictive training set. In one embodiment, the invention as disclosed herein is a method for predicting the risk of metastasis of a primary cutaneous melanoma tumor, the method comprising: (a) measuring the gene-expression levels of at least eight genes selected from the group consisting of BAP1_varA, BAP1_varB, MGP, SPP1, CXCL14, CLCA2, S100A8, BTG1, SAP130, ARG1, KRT6B, GJA, ID2, EIF1B, S100A9, CRABP2, KRT14, ROBO1, RBM23, TACSTD2, DSC1, SPRR1B, TRIM29, AQP3, TYRP1, PPL, LTA4H, and CST6, in a sample taken from the primary cutaneous melanoma tumor, wherein measuring gene-expression levels of the at least eight genes comprises measurement of a level of fluorescence by a sequence detection system following RT-PCR; (b) determining a gene-expression profile signature comprising the gene expression levels of the at least eight genes; (c) comparing the gene-expression profile to the gene-expression profile of a predictive training set; and (d) providing an indication as to whether the primary cutaneous melanoma tumor has a low risk to high of metastasis when the gene expression profile indicates that expression levels of at least eight genes are altered in a predictive manner as compared to the gene expression profile of the predictive training set.

In an additional embodiment, the invention as disclosed herein is a method of treating cutaneous melanoma in a patient, comprising the steps of: (a) obtaining the gene expression level of at least one of BAP1, MGP, SPP1, CXCL14, CLCA2, S100A8, BTG1, SAP130, ARG1, KRT6B, GJA, ID2, EIF1B, S100A9, CRABP2, KRT14, ROBO1, RBM23, TACSTD2, DSC1, SPRR1B, TRIM29, AQP3, TYRP1, PPL, LTA4H, and CST6 in a sample taken from the primary cutaneous melanoma tumor, wherein measuring gene-expression levels of the at least eight genes comprises measurement of a level of fluorescence by a sequence detection system following RT-PCR; (b) comparing the gene expression level of the at least one gene to the gene-expression level the same gene or genes taken from a predictive training set; (c) making a determination as to whether the gene-expression level of the at least one gene is altered in a predictive manner; and (d) targeting the at least one gene for therapy when the determination is made in the affirmative.

Specific embodiments of the invention will become evident from the following more detailed description of certain embodiments and the claims.

DETAILED DESCRIPTION OF THE INVENTION

Figure 1:
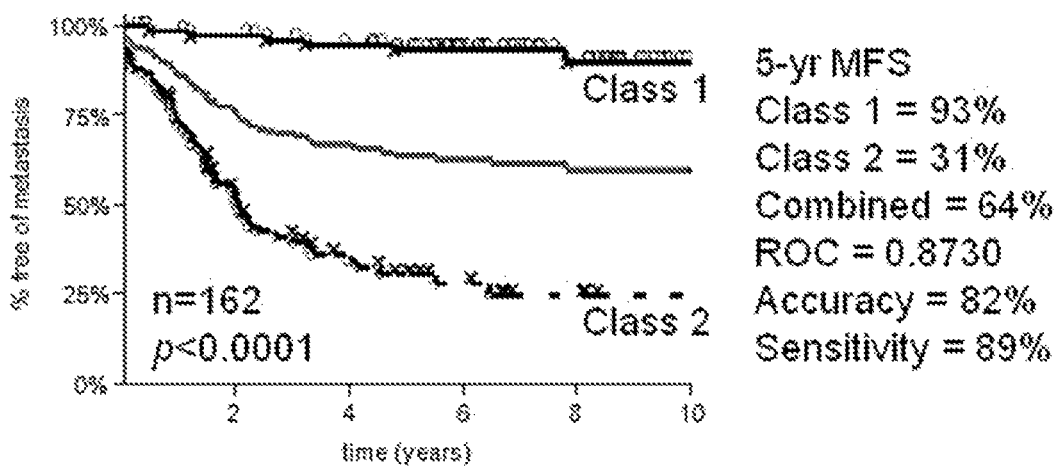
FIG. 1 depicts statistical analysis and graphs illustrating Kaplan-Meier (K-M) analysis of metastasis free survival (MFS) for CM cases predicted to be at low-risk (class 1) or high-risk (class 2) of metastasis according to a radial basis machine (RBM) modeling algorithm. 5-yr MFS for the 162 sample training set (A) is 93% for class 1 cases and 31% for class 2 cases (p<0.0001), while the entire cohort has a 5-yr MFS rate of 64%. 5-yr MFS for the independent 111 sample validation set (B) is 97% for class 1 compared to 33% for class 2 (p<0.0001), with a 69% rate in the combined cohort. Accuracy of the training set model, as measured by ROC, is 0.8730, compared to 0.9130 for the validation cohort, each reflecting clinically valuable models.
Figure 1:
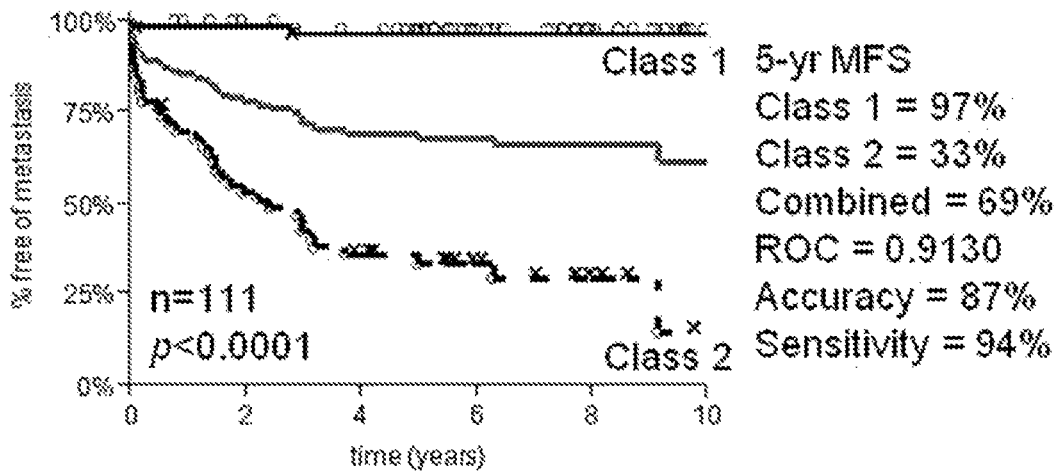

The inventors reviewed the current state of the art for evidence of microarray analyses focused on distinguishing differential genetic expression profiles that characterize cutaneous melanoma tumors. Seven studies were identified that utilized microarray technology to determine genetic expression comparing various stages of cutaneous melanoma.[22-27,29] The objective was to identify genes that were dysregulated between radial growth phase to vertical growth phase, or in primary melanomas compared to metastatic tumors. Mauerer, et. al., assessed gene expression differences in melanocytic nevi compared to primary melanoma, melanocytic nevi compared to metastatic melanoma, and primary melanoma compared to metastatic melanoma[25]. Nothing in the art was found relating to evaluation of primary cutaneous melanoma tumors relative to subsequent metastatic vs. non-metastatic outcomes. In an attempt to arrive at a putative gene expression profile set, the inventors focused on genes isolated from primary melanoma tumor samples and metastatic melanoma tumor samples that had an observed up-regulation greater than 2-fold, or down-regulation greater than 3-fold, and established those as potential mediators of metastatic progression. By these criteria, 26 up-regulated genes and 78 down-regulated genes were chosen as the basis for comparison to other expression analysis studies. This 104-gene panel was subsequently compared to expression data sets reported in Scatolini et. al., Jaeger, et. al., Winnipenninckx et. al., Haqq, et. al., Smith et. al., and Bittner et. al.[22-24,26,27,29] Additionally, the expression data from Onken, et. al., which reported 74 genes that were differentially regulated in metastatic and non-metastatic uveal melanoma tumors was compared to the 104-gene panel.[14]

In one embodiment, the invention as disclosed herein is a method for predicting the risk of metastasis of a primary cutaneous melanoma tumor, the method comprising: (a) measuring the gene-expression levels of at least eight genes selected from the group consisting of BAP1_var_A, BAP1_var_B, MGP, SPP1, CXCL14, CLCA2, S100A8, BTG1, SAP130, ARG1, KRT6B, GJA, ID2, EIF1B, S100A9, CRABP2, KRT14, ROBO1, RBM23, TACSTD2, DSC1, SPRR1B, TRIM29, AQP3, TYRP1, PPL, LTA4H, and CST6, in a sample taken from the primary cutaneous melanoma tumor, wherein measuring gene-expression levels of the at least eight genes comprises measurement of a level of fluorescence by a sequence detection system following RT-PCR; (b) determining a gene-expression profile signature comprising the gene expression levels of the at least eight genes; (c) comparing the gene-expression profile to the gene-expression profile of a predictive training set; and (d) providing an indication as to whether the primary cutaneous melanoma tumor is class 1 (low risk) or class 2 (high risk) of metastasis when the gene expression profile indicates that expression levels of at least eight genes are altered in a predictive manner as compared to the gene expression profile of the predictive training set.

In another embodiment, the invention as disclosed herein is a method of treating cutaneous melanoma in a patient, comprising the steps of: (a) obtaining the gene expression level of at least one of BAP1_varA, BAP1_varB, MGP, SPP1, CXCL14, CLCA2, S100A8, BTG1, SAP130, ARG1, KRT6B, GJA, ID2, EIF1B, S100A9, CRABP2, KRT14, ROBO1, RBM23, TACSTD2, DSC1, SPRR1B, TRIM29, AQP3, TYRP1, PPL, LTA4H, and CST6 in a sample taken from the primary cutaneous melanoma tumor, wherein measuring gene-expression levels of the at least eight genes comprises measurement of a level of fluorescence by a sequence detection system following RT-PCR; (b) comparing the gene expression level of the at least one gene to the gene-expression level the same gene or genes taken from a predictive training set; (c) making a determination as to whether the gene-expression level of the at least one gene is altered in a predictive manner; and (d) targeting the at least one gene for therapy when the determination is made in the affirmative.

In an additional embodiment, the invention as disclosed herein is a method for predicting the risk of metastasis of a primary cutaneous melanoma tumor, the method comprising: (a) measuring the gene-expression levels of at least eight genes selected from the group consisting of BAP1_varA, BAP1_varB, MGP, SPP1, CXCL14, CLCA2, S100A8, BTG1, SAP130, ARG1, KRT6B, GJA, ID2, EIF1B, S100A9, CRABP2, KRT14, ROBO1, RBM23, TACSTD2, DSC1, SPRR1B, TRIM29, AQP3, TYRP1, PPL, LTA4H, and CST6, in a sample taken from the primary cutaneous melanoma tumor, wherein measuring gene-expression levels of the at least eight genes comprises measurement of a level of fluorescence by a sequence detection system following RT-PCR; (b) determining a gene-expression profile signature comprising the gene expression levels of the at least eight genes; (c) comparing the gene-expression profile to the gene-expression profile of a predictive training set; and (d) providing an indication as to whether the primary cutaneous melanoma tumor is class A (low risk), class B (intermediate risk), or class C (high risk) of metastasis when the gene expression profile indicates that expression levels of at least eight genes are altered in a predictive manner as compared to the gene expression profile of the predictive training set.

In one embodiment, the invention as disclosed herein is a method for predicting the risk of metastasis of a primary cutaneous melanoma tumor, the method comprising: (a) measuring the gene-expression levels of at least eight genes selected from the group consisting of BAP1_varA, BAP1_varB, MGP, SPP1, CXCL14, CLCA2, S100A8, BTG1, SAP130, ARG1, KRT6B, GJA, ID2, EIF1B, S100A9, CRABP2, KRT14, ROBO1, RBM23, TACSTD2, DSC1, SPRR1B, TRIM29, AQP3, TYRP1, PPL, LTA4H, and CST6, in a sample taken from the primary cutaneous melanoma tumor, wherein measuring gene-expression levels of the at least eight genes comprises measurement of a level of fluorescence by a sequence detection system following RT-PCR; (b) determining a gene-expression profile signature comprising the gene expression levels of the at least eight genes; (c) comparing the gene-expression profile to the gene-expression profile of a predictive training set; and (d) providing an indication as to whether the primary cutaneous melanoma tumor has a low risk to high of metastasis when the gene expression profile indicates that expression levels of at least eight genes are altered in a predictive manner as compared to the gene expression profile of the predictive training set.

As used here in, "metastasis" is defined as the recurrence or disease progression that may occur locally (such as local recurrence and in transit disease), regionally (such as nodal micrometastasis or macrometastasis), or distally (such as brain, lung and other tissues). "Class 1 or class 2 of metastasis" as defined herein includes low-risk (class 1) or high-risk (class 2) of metastasis according to any of the statistical methods disclosed herein, Additionally, "cutaneous melanoma metastasis" as used herein includes sentinel lymph node metastasis, in transit metastasis, distant metastasis, and local recurrence.

As used herein, a "sequence detection system" is any computational method in the art that can be used to analyze the results of a PCR reaction. One example, inter alia, is the Applied Biosystems HT7900 fast Real-Time PCR system. In certain embodiments, gene expression can be analyzed using, e.g., direct DNA expression in microarray, Sanger sequencing analysis, Northern blot, the Nanostring® technology, serial analysis of gene expression (SAGE), RNA-seq, tissue microarray, or protein expression with immunohistochemistry or western blot technique.

As defined herein, "gene-expression profile signature" is any combination of genes, the measured messenger RNA transcript expression levels or direct DNA expression levels or immunohistochemistry levels of which can be used to distinguish between two biologically different corporal tissues and/or cells and/or cellular changes. In certain embodiments, gene-expression profile signature is comprised of the gene-expression levels of at least 28, 27, 26, 25, 24, 23, 22, 21, 20, 19, 18, 17, 16, 15, 14, 13, 12, 11, 10, 9, or 8 genes. In a further embodiments, the genes selected are KRT6B, GJA1, AQP3, TRIM29, TYRP1, RBM23, MGP and EIF1B; SAP130, ARG1, KRT6B, EIF1B, S100A9, KRT14, ROBO1, RBM23, TRIM29, AQP3, TYRP1 and CST6; GJA1, PPL, ROBO1, MGP, TRIM29, AQP3, RBM23, TACSTD2, TYRP1, KRT6B, EIF1B and DSC1; CRABP2, TYRP1, PPL, EIF1B, SPRR1B, DSC1, GJA1, AQP3, MGP, RBM23, CLCA2 and TRIM29; RBM23, TACSTD2, CRABP2, PPL, GJA1, SPP1, CXCL14, EIF1B, AQP3, MGP, LTA4H and KRT6B; S100A8, TACSTD2, BAP1_varA, KRT6B, EIF1B, TRIM29, TYRP1, CST6, PPL, RBM23, AQP3, GJA1, SPRR1B and ARG1; CST6, KRT6B, LTA4H, CLCA2, CRABP2, TRIM29, CXCL14, PPL, ARG1, RBM23, GJA1, AQP3, TYRP1, SPP1, DSC1, TACSTD2, EIF1B, and BAP1_varB.

As defined herein, "predictive training set" means a cohort of CM tumors with known clinical metastatic outcome and known genetic expression profile, used to define/establish all other CM tumors, based upon the genetic expression profile of each, as a low-risk, class 1 tumor type or a high-risk, class 2 tumor type. Additionally, included in the predictive training set is the definition of "threshold points" points at which a classification of metastatic risk is determined, specific to each individual gene expression level.

As defined herein, "altered in a predictive manner" means changes in genetic expression profile that predict metastatic risk.

In one embodiment, the cutaneous melanoma tumor is taken from a formalin-fixed, paraffin embedded wide local excision sample. In another embodiment, the cutaneous melanoma tumor is taken from formalin-fixed, paraffin embedded punch biopsy sample.

In certain embodiments, analysis of genetic expression and determination of outcome is carried out using radial basis machine and/or partition tree analysis, LRA, K-nearest neighbor, or other algorithmic approach. These analysis techniques take into account the large number of samples required to generate a training set that will enable accurate prediction of outcomes as a result of cut-points established with an in-process training set or cut-points defined for non-algorithmic analysis, but that any number of linear and nonlinear approaches can produce a statistically significant and clinically significant result. Among the advantages of use of the methods disclosed herein are relating to, e.g., the in excess of 140 samples in the training set used to cover either heterogeneity or adequately handle smaller gene expression profile changes that could not adequately predict outcomes in an independent test set. As defined herein, "Kaplan-Meier survival analysis" is understood in the art to be also known as the product limit estimator, which is used to estimate the survival function from lifetime data. In medical research, it is often used to measure the fraction of patients living for a certain amount of time after treatment. "JMP Genomics® software" provides an interface for utilizing each of the predictive modeling methods disclosed herein, and should not limit the claims to methods performed only with JMJP Genomics® software.

EXAMPLES

The Examples that follow are illustrative of specific embodiments of the invention, and various uses thereof. They are set forth for explanatory purposes only, and should not be construed as limiting the scope of the invention in any way.

Materials and Methods

1. Cutaneous Melanoma Tumor Sample Preparation and RNA Isolation

Formalin fixed paraffin embedded (FFPE) primary cutaneous melanoma tumor specimens arranged in 5 μm sections on microscope slides were acquired from multiple institutions under Institutional Review Board (IRB) approved protocols. All tissue was reviewed by a pathologist and sections with <60% tumor in an area compatible with dissection were excluded from the study. Tissue with >60% tumor were marked and tumor tissue was dissected from the slide using a sterile disposable scalpel, collected into a microcentrifuge tube, and deparaffinized using xylene. RNA was isolated from each specimen using the Ambion RecoverAll Total Nucleic Acid Isolation Kit (Life Technologies Corporation, Grand Island, NY). RNA quantity and quality were assessed using the NanoDrop 1000 system and the Agilent Bioanalyzer 2100.

2. cDNA Generation and RT-PCR Analysis

RNA isolated from FFPE samples was converted to cDNA using the Applied Biosystems High Capacity cDNA Reverse Transcription Kit (Life Technologies Corporation, Grand Island, NY). Prior to performing the RT-PCR assay each cDNA sample underwent a 14-cycle pre-amplification step. Pre-amplified cDNA samples were diluted 20-fold in TE buffer. 50 ul of each diluted sample was mixed with 50 ul of 2× TaqMan Gene Expression Master Mix, and the solution was loaded to a custom high throughput microfluidics gene card containing primers specific for 28 class discriminating genes and 3 endogenous control genes. Each sample was run in triplicate. The gene expression profile test was performed on an Applied Biosystems HT7900 machine (Life Technologies Corporation, Grand Island, NY).

3. Expression Analysis and Class Assignment

Mean $C_t$ values were calculated for triplicate sample sets, and $\Delta C_t$ values were calculated by subtracting the mean $C_t$ of each discriminating gene from the geometric mean of the mean $C_t$ values of all three endogenous control genes. $\Delta C_t$ values were standardized according to the mean of the expression of all discriminant genes with a scale equivalent to the standard deviation. Three control genes were selected based upon analysis using geNorm. Various linear and non-linear predictive modeling methods, including radial basis machine, k-nearest neighbor, partition tree, logistic regression, discriminant analysis and distance scoring, were performed using JMP Genomics SAS-based software (JMP, Cary, NC). Kaplan-Meier curves reflecting metastasis free survival were also generated in JMP, and statistical significance was calculated according to the Log Rank method. Cox univariate and multivariate regression analysis was performed using WinSTAT for Microsoft Excel version 2012.1.

Example 1: Cutaneous Melanoma Metastatic Risk Genetic Signature and Biomarker Expression Genetic expression of the discriminant genes in the signature (Table 1) was assessed in a cohort of 273 cutaneous melanoma samples using RT-PCR (FIG. 1). As shown in Table 2 below, of the 28 discriminating genes, 26 were significantly altered in metastatic melanoma tumors compared to nonmetastatic tumors (p<0.05, range 0.0366-6.08E-16), and 25 were down-regulated. Genes that were up-regulated in the metastatic tumors included SPP1, KRT6B, and EIF1B.

TABLE 1

Genes included in the GEP signature able to predict metastatic risk from primary CM tumors.

| Gene Symbol | Gene Title | Gene Title Synonyms |
|---|---|---|
| BAP1_varA | BRCA1 associated protein-1 | TPDS, UCHL2, HUCEP-13, hucep-6, BAP1 (a1), BAP1_var1 |
| MGP | Matrix Gla protein | GIG36, MGLAP, NTI |
| SPP1 | secreted phosphoprotein 1 | PSEC0156, BNSP, BSPI, ETA-1, OPN |
| CXCL14 | chemokine (C-X-C motif) ligand 14 | UNQ240/PRO273, BMAC, BRAK, KEC, KS1, MIP-2g, MIP2G, NJAC, SCYB14 |
| BAP1_varB | BRCA1 associated protein-1 | TPDS, UCHL2, HUCEP-13, hucep-6; BAP1 (a2), BAP1_var2 |
| CLCA2 | chloride channel accesory 2 | CACC, CACC3, CLCRG2, CaCC-3 |
| S100A8 | S100 calcium binding protein A8 | 60B8AG, CAGA, CFAG, CGLA, CP-10, L1Ag, MA387, MIF, MRP8, NIF, P8 |
| BTG1 | B-cell translocation gene 1, anti-proliferative | |
| SAP130 | Sin3A-associated protein, 130 kDa | |
| ARG1 | arginase, liver | |
| KRT6B | keratin 6B | CK-6B, CK6B, K6B, KRTL1, PC2 |

TABLE 1-continued

Genes included in the GEP signature able to predict metastatic risk from primary CM tumors.

| Gene Symbol | Gene Title | Gene Title Synonyms |
|---|---|---|
| GJA1 | gap junction protein, alpha 1 | AU042049, AW546267, Cnx43, Cx43, Cx43alpha1, Gja-1, Npm1, connexin43 |
| ID2 | inhibitor of DNA binding 2 | AI255428, C78922, Idb2, bHLHb26 |
| EIF1B | eukaryotic translation initiation factor 1B | GC20 |
| S100A9 | S100 calcium binding protein A9 | 60B8AG, CAGB, CFAG, CGLB, L1AG, LIAG, MAC387, MIF, MRP14, NIF, P14 |
| CRABP2 | cellular retinoic acid binding protein 2 | RP11-66D17.4, CRABP-II, RBP6 |
| KRT14 | keratin 14 | CK14, EBS3, EBS4, K14, NFJ |
| ROBO1 | roundabout, axon guidance receptor, homolog 1 (*Drosophila*) | DUTT1, SAX3 |
| RBM23 | RNA binding motif protein 23 | PP239, CAPERbeta, RNPC4 |
| TACSTD2 | tumor-associated calcium signal transducer 2 | EGP-1, EGP1, GA733-1, GA7331, GP50, M1S1, TROP2 |
| DSC1 | desmocollin 1 | CDHF1, DG2/DG3 |
| SPRR1B | small proline-rich protein 1B | CORNIFIN, GADD33, SPRR1 |
| TRIM29 | tripartite motif containing 29 | ATDC |
| AQP3 | aquaporin 3 | AQP-3, GIL |
| TYRP1 | tyrosinase-related protein 1 | RP11-3L8.1, CAS2, CATB, GP75, OCA3, TRP, TRP1, TYRP, b-PROTEIN |
| PPL | periplakin | |
| LTA4H | leukotriene A4 hydrolase | |
| CST6 | cystatin E/M | |

TABLE 2

Genes included in the GEP signature able to predict metastatic risk from primary CM tumors.

| | ΔCt value | | expression | | |
|---|---|---|---|---|---|
| Gene symbol | nonmetastatic samples | metastatic samples | change in metastatic samples | p-value | direction of expression change |
| BAP1_varA | −1.290 | −1.677 | −0.388 | 0.007118 | down |
| MGP | −1.996 | −2.190 | −0.194 | 0.48585 | down |
| SPP1 | −1.011 | 2.224 | 3.235 | 6.08E−16 | up |
| CXCL14 | 3.021 | 0.828 | −2.193 | 3.31E−12 | down |
| BAP1_varB | 0.381 | 0.003 | −0.378 | 0.004646 | down |
| CLCA2 | −3.468 | −5.603 | −2.135 | 1.02E−08 | down |
| S100A8 | −0.450 | −1.179 | −0.728 | 0.030655 | down |
| BTG1 | −2.422 | −3.008 | −0.586 | 0.023606 | down |
| SAP130 | −1.075 | −1.405 | −0.329 | 0.023626 | down |
| ARG1 | −1.645 | −4.393 | −2.749 | 1.05E−08 | down |
| KRT6B | −1.809 | −1.222 | 0.586 | 0.160458 | up |
| GJA1 | −2.882 | −3.652 | −0.770 | 0.034149 | down |
| ID2 | −0.649 | −1.411 | −0.762 | 3.91E−06 | down |
| EIF1B | 0.041 | 0.350 | 0.309 | 0.023747 | up |
| S100A9 | 3.374 | 2.527 | −0.847 | 0.012385 | down |
| CRABP2 | −0.087 | −0.953 | −0.866 | 0.00059 | down |
| KRT14 | 5.654 | 3.927 | −1.727 | 1.75E−05 | down |
| ROBO1 | 0.100 | −0.364 | −0.464 | 0.000406 | down |
| RBM23 | −2.788 | −3.161 | −0.374 | 0.018025 | down |
| TACSTD2 | −3.485 | −3.984 | −0.499 | 0.03658 | down |
| DSC1 | −0.102 | −2.963 | −2.861 | 7E−09 | down |
| SPRR1B | 4.622 | 3.139 | −1.482 | 0.001392 | down |
| TRIM29 | 0.228 | −2.239 | −2.467 | 2.34E−09 | down |
| AQP3 | 3.413 | 1.848 | −1.565 | 5.08E−06 | down |
| TYRP1 | 1.276 | −0.850 | −2.125 | 2.41E−06 | down |
| PPL | −0.082 | −2.233 | −2.150 | 5.59E−11 | down |
| LTA4H | −0.736 | −1.275 | −0.539 | 0.000156 | down |
| CST6 | −0.535 | −3.099 | −2.563 | 1.02E−08 | down |

Example 2: Initial Training Set Development Studies and Comparison to Validation Cohort Using JMP Genomics® software and clinical data analysis, a training set of 162 cutaneous melanoma samples was generated that could accurately predict the risk of metastasis based upon the 28 gene signature. The training set contained 13 stage 0 in situ melanomas, 61 stage I, 70 stage II, 17 stage III, and 1 stage IV melanomas. Metastatic risk was assessed using a radial basis machine predictive modeling algorithm, which reports class 1 (low risk of metastasis) or class 2 (high risk of metastasis). ΔCt values generated from RT-PCR analysis of the training set cohort were standardized to the mean for each gene, with a scale equivalent to the standard deviation. Analyses were also performed using KNN, PTA, and discriminant analysis to confirm the results from the RBM approach (as discussed below). The training set prediction algorithm was then validated using an independent cohort of 111 cutaneous melanoma samples, comprised of four stage 0 in situ melanomas, 56 stage I, 36 stage II, 12 stage III, and 2 stage IV melanomas. Samples in the validation set were standardized prior to analysis using the factorials generated during standardization of the training set. Area under the receiver operator characteristic (ROC) curve, accuracy, sensitivity (prediction of high risk metastatic event), and specificity (prediction of nonmetastatic outcome) were statistical endpoints for the analysis. In the training set cohort, ROC=0.8730, accuracy=82%, sensitivity=89%, and specificity=74% (FIG. 1A). In the validation cohort, ROC=0.9130, accuracy=87%, sensitivity=94%, and specificity=79% (FIG. 1B).

Kaplan-Meier survival analysis was also performed for the training and validation cohorts. In the training set, 5-year metastasis free survival (MFS) was 93% for class 1 cases, and 31% for class 2 cases (p<0.0001; FIG. 1A). By comparison, 5-year MFS for the validation cohort was 97% for class 1 cases and 33% for class 2 cases (p<0.0001; FIG. 1). Overall, the 5-year MFS rate for the entire training set, combining class 1 and class 2 cases, was 64%, while the combined MFS rate for the validation set was 69%.

Figure 2:
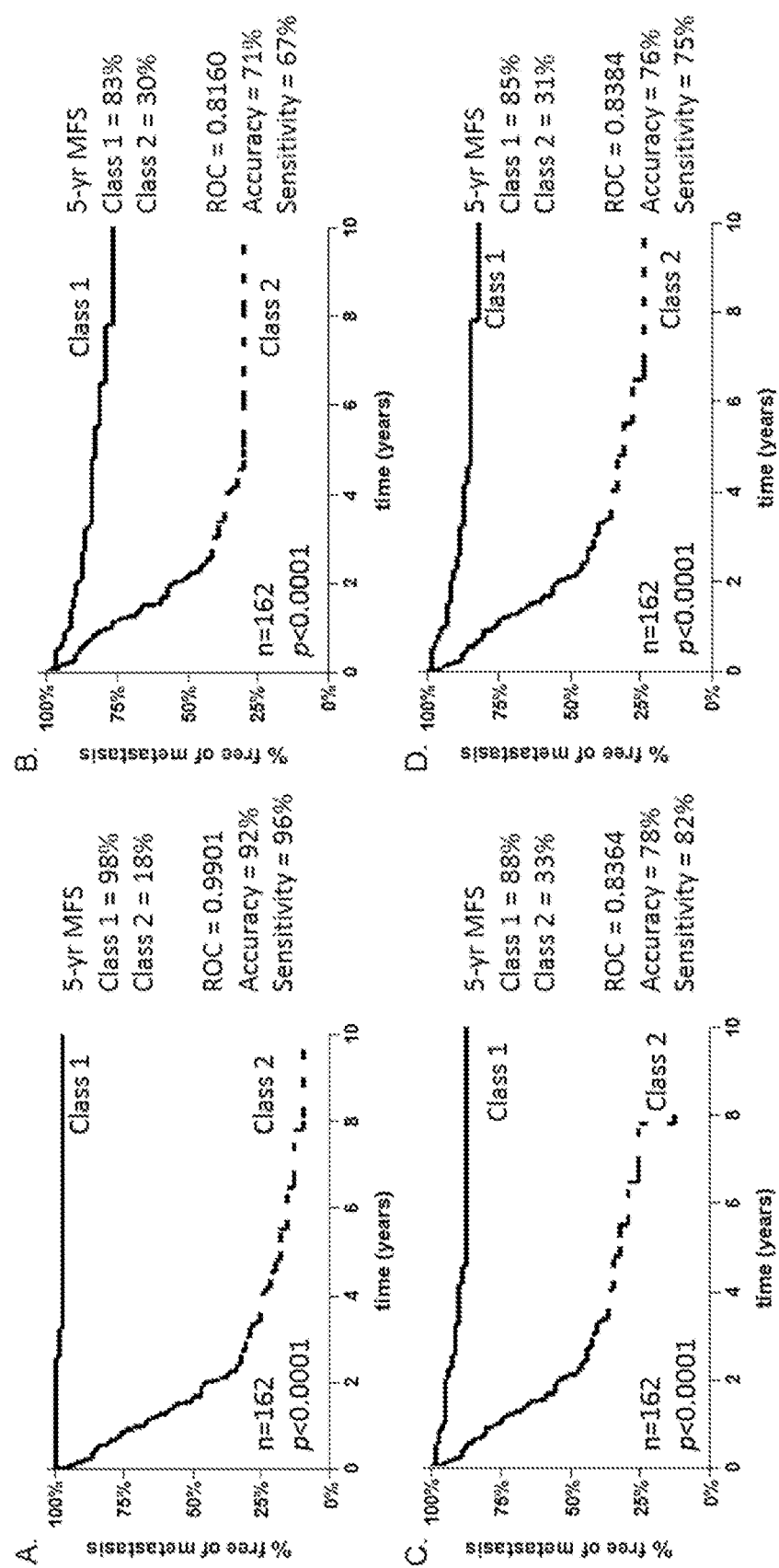
FIG. 2 depicts statistical and K-M analysis of the 162 sample training set when metastasis is predicted using partition tree (A), K-nearest neighbor (B), logistic regression (C), or discriminant analysis (D) modeling algorithms. Highly significant differences in K-M MFS curves for class 1 and class 2 cohorts are observed with each modeling method. Accuracy is highest when analysis is performed with the partition tree model (ROC=0.9901; accuracy=92%; sensitivity=96%), while the other models are also statistically accurate, with ROC>0.8.
Figure 3:
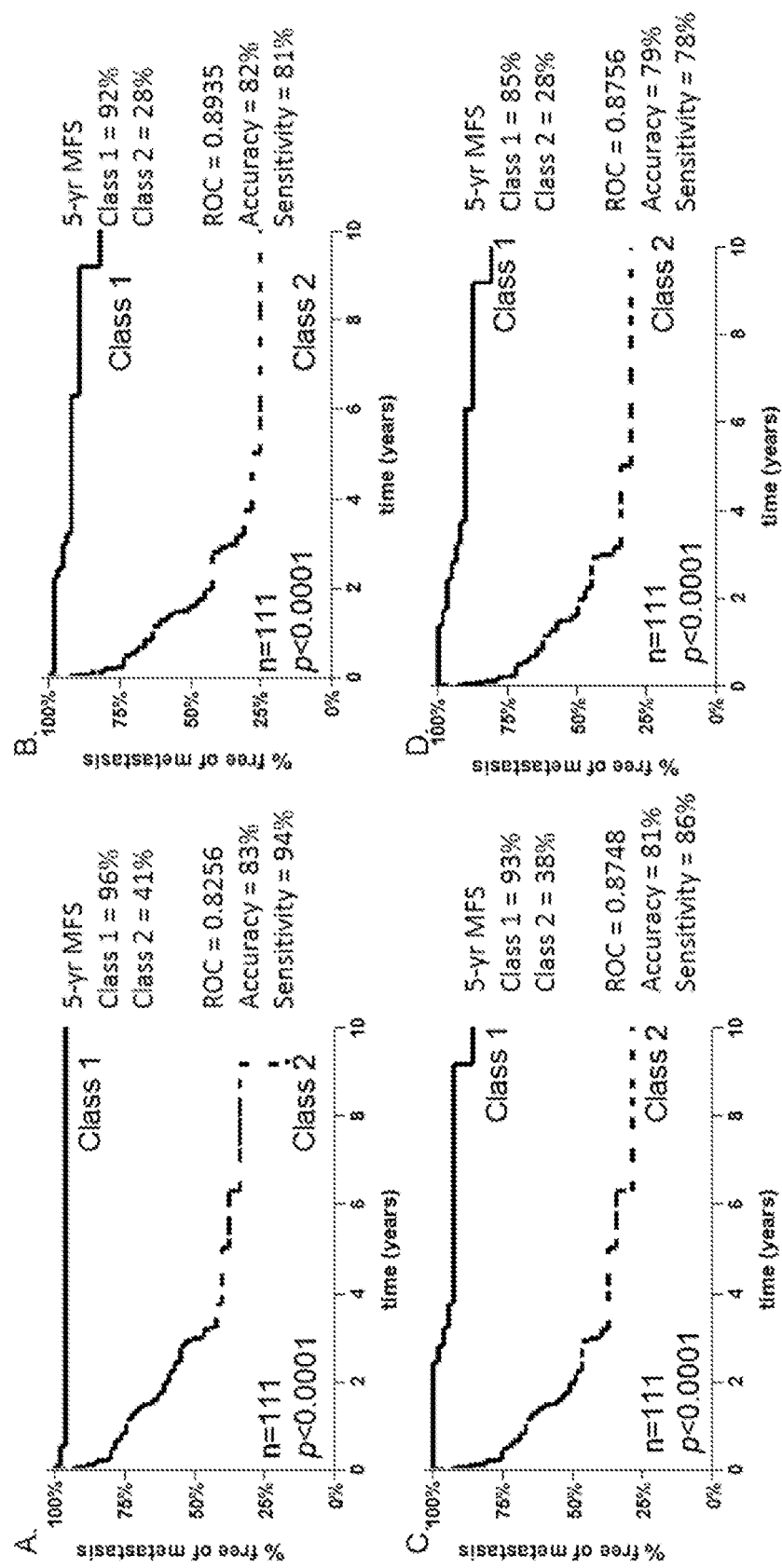
FIG. 3 depicts the same statistics and graphs as FIG. 2, but with partition tree (A), K-nearest neighbor (B), logistic regression (C), or discriminant analysis (D) used to analyze the independent 111 sample validation set. Significant differences between class 1 and class 2 K-M curves are observed using each modeling method. Algorithm accuracy is highest for the K-nearest neighbor model (ROC=0.8935), while the highest sensitivity, or accuracy of predicting class 2 high risk cases, was observed when using the partition tree model (sensitivity=94%). 4

Example 3: Analysis of 162 Sample Training Set with Multiple Predictive Modeling Methods JMP® Genomics software allows for analysis using linear and non-linear predictive modeling methods. To assess whether accuracy of metastatic risk prediction for the validation cohort was limited to the RBM method, partition tree, K-nearest neighbor, logistic regression, and discriminant analysis were performed (FIGS. 2 and 3). Training set ROC, accuracy, sensitivity, specificity and K-M 5-year MFS for class 1 and class 2 cases were highly comparable to the RBM method. Highly accurate prediction of metastasis, and significantly different 5-year MFS between class 1 and class 2 cases was observed when using partition tree (FIG. 2A), K-nearest neighbor (FIG. 2B), logistic regression (FIG. 2C), or discriminant analysis (FIG. 2D). Significant differences in 5-year MFS were also observed for validation cohort class 1 and class 2 cases using partition tree (FIG. 3A), K-nearest neighbor (FIG. 3B), logistic regression (FIG. 3C), and discriminant analysis (FIG. 3D). Importantly, though, accuracy of prediction for validation samples was above 80% with all methods except discriminant analysis (FIG. 3D), and sensitivity, or accuracy of prediction for cases with documented metastatic events, was as high as 94% when using partition tree analysis.

Example 4: Evaluation of In Situ Melanoma Effect Upon Training Set Accuracy

Figure 4:
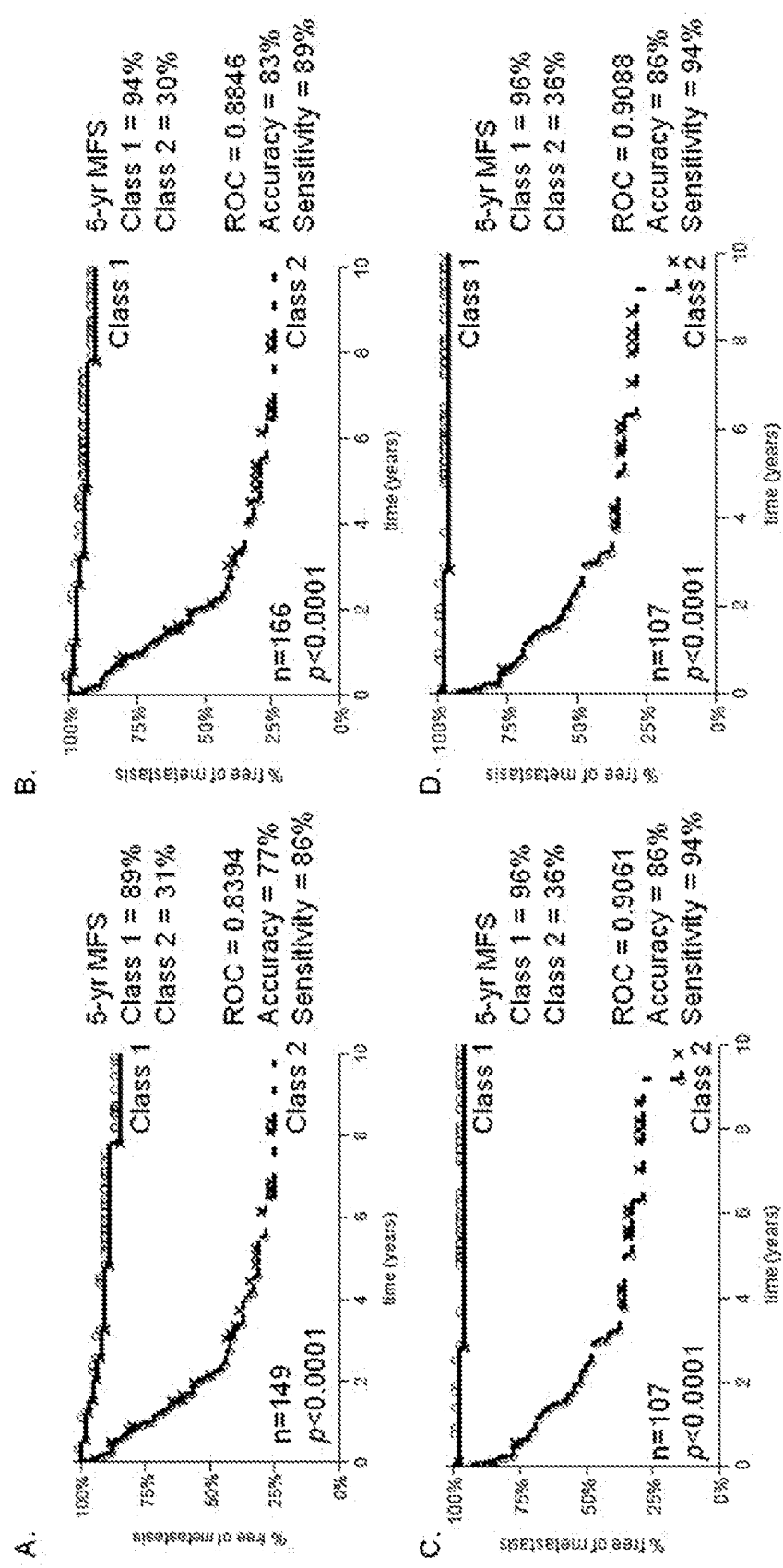
FIG. 4 depicts statistics and K-M analysis reflecting the impact of stage 0 in situ melanomas on training set predictive power. Removing stage 0 cases from the original training and validation cohorts produces a 149 sample training set (A) and independent 107 sample validation set (C). Significant differences are observed in class 1 and class 2 K-M curves for both cohorts (p<0.0001), and metastatic risk prediction is accurate in both the training and validation sets (ROC=0.8394 and 0.9061, respectively). Analysis was also performed following inclusion of all stage 0 samples in the training set, producing a training cohort of 166 samples (B) that exhibited better accuracy (ROC=0.8846; Accuracy=83%; sensitivity=89%) compared to the 149 sample training set. No dramatic differences are observed when the independent 107 sample validation set is trained using the 166 sample cohort (D) compared to (C).

To assess the impact of stage 0 in situ melanoma samples on the predictive capabilities of the training set, either a) samples were removed from all stage 0 the training and validation cohorts, generating a new training set of 149 cases; or b) all stage 0 samples were included in the training set only, generating a training set comprised of 166 cases. The new cutaneous melanoma predictive training sets were used to train a 107 sample validation cohort (the 111 sample validation set tested to this point, with four stage 0 in situs removed).
Radial basis machine prediction was performed as described above, and ROC, accuracy of prediction, and 5-year MFS were assessed for the training and validation sets (FIG. 4). Training set statistics for both the 149 sample and 166 sample training sets (FIGS. 4A and 4B) were highly comparable to the 162 sample training set. ROC was highest for the 166 sample set, but accuracy, sensitivity and specificity were identical in the 162 and 166 sample training sets. K-M analysis yielded highly significant differences between class 1 and class 2 MFS with each training set. Metastatic risk of the 107 samples in the validation cohort was accurately predicted with the 149 and 166 sample training sets (FIGS. 4C and 4D). Similar to the results seen for the validation set trained with the 162 sample cohort, both validation sets had ROC greater than 0.9, reflecting highly relevant clinical models of prediction, and sensitivity of 94%. Again, MFS was significantly different between class 1 and class 2 regardless of the training set cohort used to predict risk in the validation set.

Example 5: Identification of Reduced Discriminant Gene Signatures with Predictive Accuracy Accurate prediction of high risk metastatic cases is extremely important in order to prevent those patients who are likely to metastasize from receiving a low risk treatment protocol. Thus, a measure of success for the predictive gene set is achievement of greater than 88% sensitivity in both the training and validation sets. As shown in Table 3 below, and in FIG. 4, sensitivity is 89% for the 166 sample training set and 94% for the 107 sample validation set when the 28-gene signature incorporating all discriminant genes is used to predict metastatic risk. Smaller sets of genes were generated that had equal or increased sensitivity compared to the 28-gene signature (Table 3, bolded). However, the majority of gene sets that did not include all 28 genes were not able to produce the sensitivity thresholds required for use in a clinically feasible GEP test.

TABLE 3

Sensitivity, or accuracy of predicting a metastatic event, achieved when using the 28-gene signature or smaller subsets of genes.

| Gene set | # of variables | Sensitivity training/validation sets (%) |
|---|---|---|
| all discriminant genes | 28 | 89/94 |
| SPP1, CXCL14, BAP1_varA, CLCA2, S100A8, BTG1 | 6 | 79/89 |
| TACSTD2, RBM23, PPL, S100A8, MGP, TYRP1 | 6 | 86/78 |
| SAP130, ARG1, KRT6B, GJA1, EIF1B, ID2 | 6 | 81/81 |
| CRABP2, KRT14, ROBO1, RBM23, TACSTD2, DSC1 | 6 | 70/81 |
| ROBO1, CST6, BAP1_varB, ID2, SPRR1B, KRT6B | 6 | 75/83 |
| SPRR1B, AQP3, PPL, DSC1, TYRP1, TRIM29 | 6 | 81/81 |
| KRT6B, GJA1, AQP3, TRIM29, TYRP1, RBM23, MGP, EIF1B | 8 | 93/94 |
| SPP1, MGP, KRT6B, PPL, RBM23, AQP3, CXCL14, GJA1 | 8 | 86/92 |
| BAP1_varB, S100A8, ARG1, S100A9, RBM23, DSC1, TYRP1, CST6 | 8 | 77/94 |
| BAP1_varA, BTG1, ARG1, GJA1, EIF1B, TACSTD2, TYRP1, LTA4H | 8 | 74/89 |
| GJA1, ID2, KRT14, ROBO1, RBM23, TRIM29, LTA4H, S100A9 | 8 | 70/69 |
| DSC1, SPRR1B, TRIM29, AQP3, TYRP1, PPL, LTA4H, CST6 | 8 | 72/86 |
| KRT14, ROBO1, RBM23, TACSTD2, DSC1, SPRR1B, TRIM29, AQP3 | 8 | 68/72 |
| BAP1_varA, MGP, SPP1, CXCL14, BAP1_varB, CLCA2, S100A8, BTG1 | 8 | 81/83 |
| SAP130, ARG1, KRT6B, GJA1, EIF1B, ID2, EIF1B, S100A9, CRABP2 | 8 | 84/81 |
| MGP, SAP130, GJA1, ID2, S100A9, ROBO1, AQP3, LTA4H | 8 | 65/69 |
| SAP130, ARG1, KRT6B, EIF1B, S100A9, KRT14, ROBO1, RBM23, TRIM29, AQP3, TYRP1, CST6 | 12 | 91/97 |
| GJA1, PPL, ROBO1, MGP, TRIM29, AQP3, RBM23, TACSTD2, TYRP1, KRT6B, EIF1B, DSC1 | 12 | 93/94 |

TABLE 3-continued

Sensitivity, or accuracy of predicting a metastatic event, achieved when using the 28-gene signature or smaller subsets of genes.

| Gene set | # of variables | Sensitivity training/validation sets (%) |
|---|---|---|
| CRABP2, TYRP1, PPL, EIF1B, SPRR1B, DSC1, GJA1, AQP3, MGP, RBM23, CLCA2, TRIM29 | 12 | 93/89 |
| RBM23, TACSTD2, CRABP2, PPL, GJA1, SPP1, CXCL14, EIF1B, AQP3, MGP, LTA4H, KRT6B | 12 | 91/89 |
| BAP1_varA, SPP1, BAP1_varB, S100A8, SAP130, KRT6B, ID2, S100A9, ROBO1, TACSTD2 | 12 | 86/83 |
| BAP1_varA, MGP, S100A8, BTG1, ARG1, S100A9, KRT14, ROBO1, SPRR1B, TRIM29, AQP3, LTA4H | 12 | 75/75 |
| SPP1, BAP1_varB, CLCA2, SAP130, GJA1, S100A9, RBM23, SPRR1B, TYRP1, BTG1, KRT6B | 12 | 84/89 |
| EIF1B, S100A9, CRABP2, KRT14, ROBO1, RBM23, TRIM29, AQP3, TYRP1, PPL, LTA4H, CST6 | 12 | 82/89 |
| CXCL14, BAP1_varB, CLCA2, S100A8, BTG1, SAP130, S100A9, CRABP2, KRT14, ROBO1, RMB23, TACSTD2 | 12 | 79/92 |
| MGP, CLCA2, S100A8, ARG1, GJA1, ID2, S100A9, ROBO1, RBM23, SPRR1B, TRIM29, AQP3 | 12 | 70/78 |
| S100A8, TACSTD2, BAP1_varA, KRT6B, EIF1B, TRIM29, TYRP1, CST6, PPL, RBM23, AQP3, GJA1, SPRR1B, ARG1 | 14 | 91/89 |
| BAP1_varB, CLCA2, BTG1, SAP130, GJA1, ID2, S100A9, CRABP2, RBM23, TACSTD2, DSC1, LTA4H, SPP1, KRT6B | 14 | 86/89 |
| SPP1, CLCA2, S100A8, SAP130, ARG1, ID2, EIF1B, S100A9, KRT14, ROBO1, DSC1, TRIM29, TYRP1, LTA4H | 14 | 86/97 |
| CXCL14, BAP1_varB, S100A8, BTG1, ARG1, KRT6B, ID2, EIF1B, CRABP2, KRT14, RBM23, TACSTD2, SPRR1B, TRIM29 | 14 | 89/82 |
| BAP1_varA, MGP, SPP1, CXCL14, BAP1_varB, CLCA2, S100A8, BTG1, SAP130, ARG1, KRT6B, GJA1, ID1, EIF1B | 14 | 84/86 |
| S100A9, CRABP2, KRT14, ROBO1, RBM23, TACSTD2, DSC1, SPRR1B, TRIM29, AQP3, TYRP1, PPL, LTA4H, CST6 | 14 | 82/78 |
| BTG1, SAP130, ARG1, GJA1, EIF1B, CRABP2, ROBO1, RBM23, TACSTD2, DSC1, SPRR1B, AQP3, PPL, CST6 | 14 | 84/86 |
| BAP1_varA, MGP, BAP1_varB, CLCA2, BTG1, SAP130, GJA1, ID2, S100A9, CRABP2, RBM23, TACSTD2, DSC1, LTA4H | 14 | 72/72 |
| MGP, CXCL14, S100A8, BTG1, ARG1, GJA1, ID2, S100A9, KRT14, ROBO1, TACSTD2, SPRR1B, TRIM29, TYRP1 | 14 | 82/86 |
| S100A8, BTG1, SAP130, EIF1B, S100A9, CRABP2, KRT14, DSC1, SPRR1B, TRIM29, AQP3, CST6, BAP1_varB, LTA4H | 14 | 79/86 |
| CST6, KRT6B, LTA4H, CLCA2, CRABP2, TRIM29, CXCL14, PPL, ARG1, RBM23, GJA1, AQP3, TYRP1, SPP1, DSC1, TACSTD2, EIF1B, BAP1_varA | 18 | 91/89 |
| MGP, CXCL14, CLCA2, BTG1, ARG1, GJA1, EIF1B, CRABP2, ROBO1, TACSTD2, DSC1, SPRR1B, TRIM29, AQP3, TYRP1, PPL, LTA4H, CST6 | 18 | 81/92 |
| MGP, BAP1_varB, CLCA2, S100A8, BTG1, KRT6B, GJA1, ID2, EIF1B, S100A9, ROBO1, RBM23, TACSTD2, AQP3, TYRP1, PPL, LTA4H, SPRR1B | 18 | 81/100 |

Example 6: 28-Gene Signature for Cutaneous Melanoma Predicts Aggressive Tumor Progression to SLN, Distant Lymph Nodes, in Transit Metastasis, Distant Metastasis, and Local Recurrence A total of 29 stage III, sentinel lymph node (SNL) positive, samples were included in the study population (17 in the training set and 12 in the validation set). These results are shown below in Table 4. RBM prediction of risk for the stage III samples resulted in 25 of 29 (86%) cases classified as high risk, class 2. Metastasis beyond the SLN was documented for 23 of the 29 cases, and 21 of those were predicted to be class 2 by the algorithm. Metastatic events localized to distant lymph nodes were documents for 13 cases, 12 (92%) of which were accurately predicted to be class 2. Similarly, 6 of 7 (86%) of in transit metastasis cases were assigned to class 2, indicating that the 28-gene predictive signature accurately predicts all aggressive cutaneous melanoma tumor types, including SLN positive, distant nodal, in transit, distant visceral metastases and local recurrence.

TABLE 4

Accuracy of the CM 28-gene signature for predicting metastatic risk in SLN, distant lymph nodes, in transit metastasis, and locally recurrent disease.

| | training set | | validation set | |
|---|---|---|---|---|
| | total | called class 2 | total | called class 2 |
| SLN+ (stage III) samples | 17 | 14 (82%) | 12 | 11 (92%) |
| documented met event | 12 | 11 (92%) | 11 | 10 (91%) |
| no documented met event | 5 | 3 (60%) | 1 | 1 (100%) |

TABLE 4-continued

Accuracy of the CM 28-gene signature for predicting metastatic risk in SLN, distant lymph nodes, in transit metastasis, and locally recurrent disease.

|  | training set | | validation set | |
|---|---|---|---|---|
|  | total | called class 2 | total | called class 2 |
| distant lymph node metastasis | 6 (2 SLN+) | 6 (100%) | 7 (5 SLN+) | 6 (86%) |
| in transit metastasis | 3 | 2 (66%) | 4 | 4 (100%) |
| local recurrence | 9 | 4* (44%) | 5** | 3 (60%) |

*2/4 LR have known metastatic event (both called class 2)
**1/5 LR is stage III (SLN+) - called class 2

Example 7: Statistical Comparison of GEP Signature to Common CM Prognostic Factors Cox univariate and multivariate regression analysis was performed for the 107 sample validation cohort following prediction of metastatic risk (Tables 5 and 6). GEP was compared to the individual prognostic factors comprising AJCC pathologic stage, including Breslow thickness, mitotic rate, and ulceration status, and was also compared directly to AJCC stage. AJCC stage was analyzed as known in the art as Stage IA, IB, IIA vs. IIB, IIC, III, IV for the complete validation set, and as Stage IA, IB, IIA vs. IIB, IIC for analysis that included only Stage I and II. Thus, analysis was performed with inclusion of all validation set cases (Table 5), or with inclusion of only stage I and stage II cases (Table 6). Cox univariate analysis resulted in significant correlation with metastasis for all factors except mitotic rate regardless of whether all validation set cases were included, or whether inclusion was restricted to stage I and II cases only. Comparison of GEP to Breslow thickness, ulceration, and mitotic rate showed that GEP and ulceration were significantly correlated to metastatic risk in a multivariate analysis (HR=8.4 and 2.6, p=0.04 and 0.03, respectively). Direct comparison to AJCC stage by multivariate analysis indicates that both factors are significantly correlated to metastasis (GEP HR=10.3, p<0.004; AJCC HR=6.4, p<0.0002). These results indicate that the 28-gene signature is able to predict metastasis independently of AJCC TNM staging and other prognostic factors.

TABLE 5

Univariate and multivariate analysis of cutaneous melanoma prognostic factors with inclusion of cases from all AJCC stages.

| Variable | Univariate | | | Multivariate | | |
|---|---|---|---|---|---|---|
|  | P-value | HR | CI | P-value | HR | CI |
| Breslow (0.75 mm) | 0.002 | 24 | 2.0 | 0.09 | 16 | 3.2 |
| Ulceration | <10-7 | 11.6 | 0.8 | 0.03 | 2.6 | 0.9 |
| Mitotic | 0.06 | 4.0 | 1.4 | 0.13 | 3.1 | 1.4 |
| GEP test | <10-6 | 32 | 1.4 | 0.04 | 8.4 | 2.0 |
| AJCC | <10-7 | 20 | 0.9 | 0.0002 | 6.4 | 1.0 |
| GEP test | <10-6 | 32 | 1.4 | 0.004 | 10.3 | 1.6 |

An important clinical application of the GEP test is to identify patients who are staged as low risk (clinical stage I and II) for metastasis but who are at actual high risk for metastasis based upon the genomic signature of their CM. The Cox univariate and multivariate regression analysis was performed for those patients in the 107 sample validation cohort following prediction of metastatic risk (Table 6) who had clinical stage I and II CM only. Again, GEP was compared to the elements comprising AJCC pathologic stage: Breslow thickness, mitotic rate, and ulceration status, and directly to AJCC stage. Under univariate analysis, Breslow's thickness, ulceration status and GEP Class 2 were significant (p<0.0005). However, under multivariate analysis, only GEP Class 2 was significant (Hazard ratio=27; p=0.01). Univariate analyses for comparison of AJCC stage to GEP Class 2 showed both to be statistically significant, but the GEP Class 2 variable had a greater Hazard ratio than AJCC stage (48 vs 15, respectively). Multivariate analyses demonstrated that both factors were independent of each other (p<0.006) but the Hazard Ratio for the GEP Class 2 was again greater than that of AJCC stage (23 vs. 4.0). Together, these two result tables (Table 5 and 6) indicate that the 28-gene signature predicts metastasis independently of AJCC TNM staging and other prognostic factors in patients of all stage (I, II, III and IV).

TABLE 6

Univariate and multivariate analysis of cutaneous melanoma prognostic factors with inclusion of cases from AJCC stages I and II.

| Variable | Univariate | | | Multivariate | | |
|---|---|---|---|---|---|---|
|  | P-value | HR | CI | P-value | HR | CI |
| Breslow (0.75 mm) | 0.0005 | 151 | 2.8 | 0.97 | 1.1 | 4.2 |
| Ulceration | <10-6 | 11 | 1.0 | 0.22 | 1.9 | 1.0 |
| Mitotic | 0.2 | 2.6 | 1.5 | 0.32 | 2.1 | 1.4 |
| GEP test | 0.0002 | 48 | 2.0 | 0.01 | 27 | 2.5 |
| AJCC | <10-7 | 15 | 1.0 | 0.006 | 4.0 | 1.0 |
| GEP test | 0.0002 | 48 | 2.0 | 0.004 | 23 | 2.1 |

Figure 5:
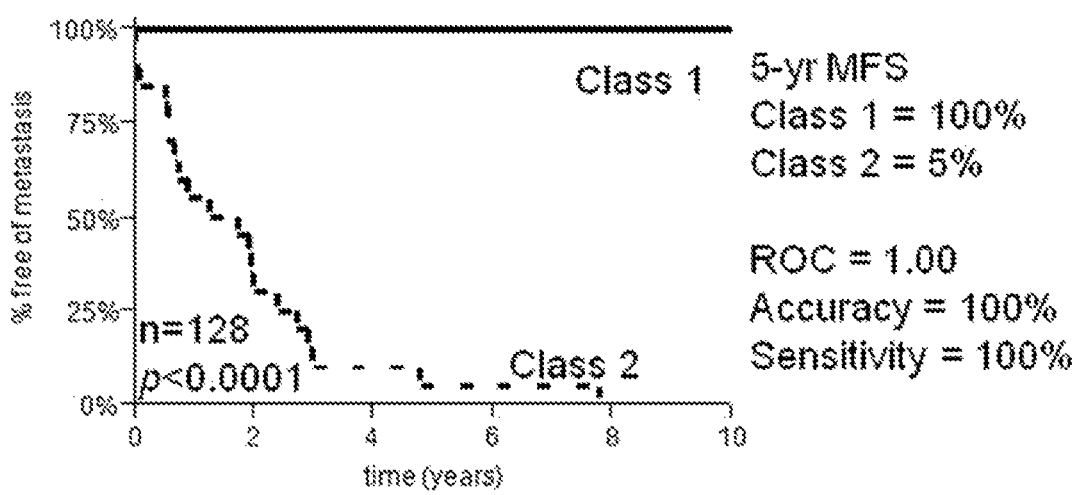
FIG. 5 depicts MFS statistics and accuracy of the genetic signature when used to predict metastatic risk in superficial spreading (A) or nodular (B) type CM tumors. K-M MFS was 100% for superficial spreading cases predicted to be class 1, and only 5% for cases predicted to be class 2 (p<0.0001). The predictive model had an accuracy of 100% for predicting both classes, and ROC=1.00. Prediction of risk for nodular tumors was less accurate, with an ROC=0.9323, accuracy of 82%, and sensitivity of 81%, but K-M analysis reflects a significant difference between the 81% 5-year MFS for Class 1 and the 7% MFS for Class 2 cases (p<0.0001).
Figure 5:
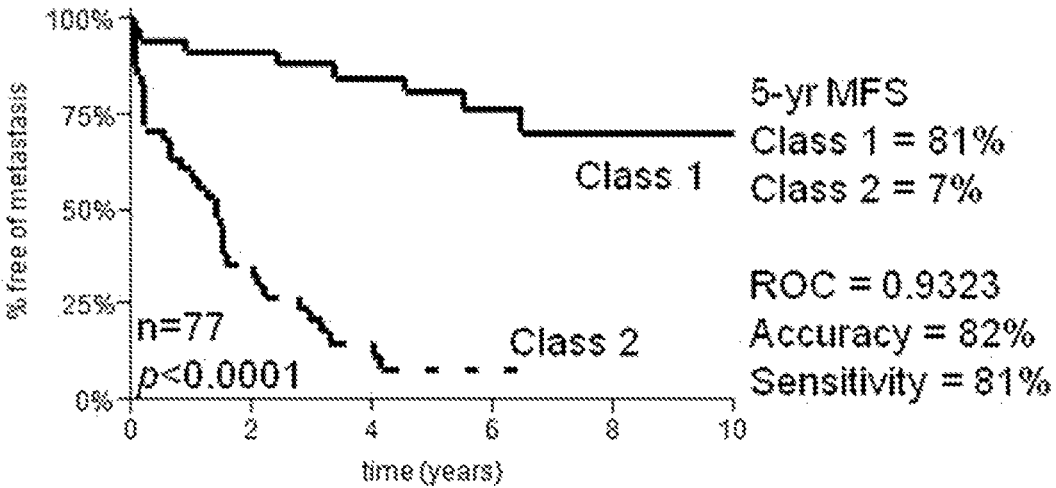

Example 8: 28-Gene Signature for Cutaneous Melanoma Predicts Metastasis in Superficial Spreading and Nodular Growth Patterns Of the four growth patterns described for CM tumors, superficial spreading is the most prevalent, and biologically distinct from nodular melanomas.[13] Radial basis machine analysis of the superficial spreading tumors within the cohort (n=128) resulted in a highly accurate classification of metastatic and non-metastatic tumors (FIG. 5A). K-M MFS analysis shows that cases predicted to be class 1 have a 100% 5-year metastasis free rate, while high risk class 2 cases have only a 5% MFS rate. Additionally, an ROC=1.00 reflects 100% accuracy of the prediction for superficial spreading tumors. The genetic signature is also able to predict metastatic potential for nodular type CM tumors (FIG. 5B). K-M MFS rate is 81% for class 1 cases, compared to 7% for class 2 cases (p<0.0001). Accuracy of the predicted model was high, as evidenced by ROC=0.9323, accuracy of 82%, and sensitivity of 81%. These results indicate that the genetic signature has high accuracy for predicting superficial spreading disease and lower accuracy for predicting nodular disease. While the invention has been described in terms of various embodiments, it is understood that variations and modifications will occur to those skilled in the art. Therefore, it is intended that the appended claims cover all such equivalent variations that come within the scope of the invention as claimed. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

Figure 6:
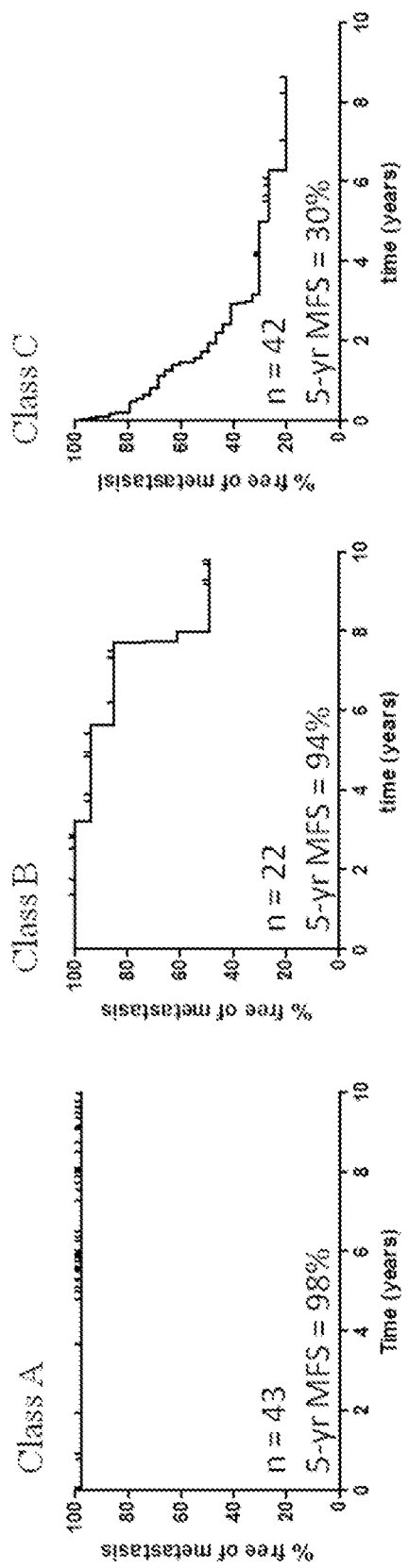
FIG. 6 depicts MFS graphs and statistical analysis following a tri-modal prediction for CM cases at low-risk (class A), intermediate risk (class B) or high-risk (class C) of metastasis according to a radial basis machine (RBM) modeling algorithm. 5-yr MFS for the independent 107 sample validation set is 98% for class A compared to 94% for class B and 30% for class C (p<0.0001), with a 64% rate in the overall cohort, reflecting clinically valuable models.

Example 9: Trimodal and Linear Methods for Predicting Metastatic Risk According to GEP While a bimodal (low risk Class 1 vs high risk Class 2) may be the preferred clinical reporting output, additional analysis suggest that the tri-modal or linear approach may be clinically appropriate. Analysis using a trimodal approach demonstrated a stratification outcome related to metastatic risk. Specifically, development of a Class A (low risk), Class B (medium risk) and Class C (high risk) trimodal output shows a graduated increase in metastatic risk (FIG. 6). Analysis shows 5-yr MFS for the independent 107 sample validation set is 98% for class A compared to 94% for class B and 30% for class C (p<0.0001), with a 64% rate in the overall cohort, reflecting clinically valuable models.

Figure 7:
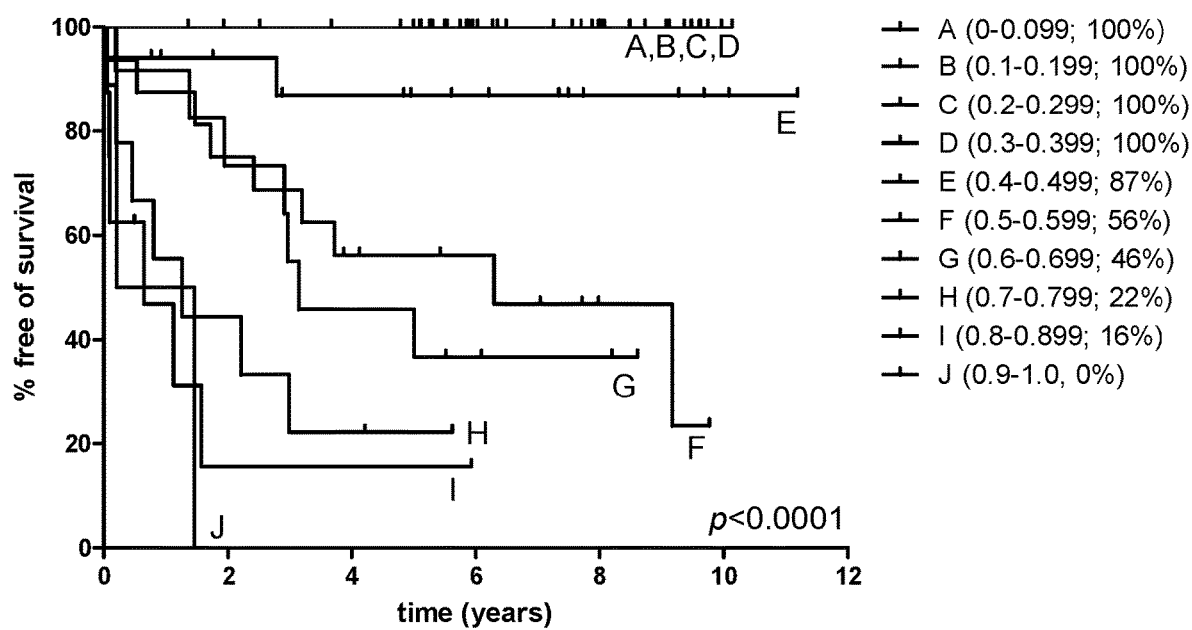
FIG. 7 depicts MFS for the 107 sample validation cohort based upon the probability score generated for each case during predictive modeling analysis. Subgroups A-J represent 0.1 unit incremental increases in the probability of metastasis (0=low risk of metastasis, 1=high risk of metastasis), as determined by the RBM algorithm. Importantly, increases in probability score correspond to decreases in MFS rates. For example, all cases in subgroup A have a probability score between 0 and 0.099, and there is 100% 5 year MFS in the cohort. Conversely, each of the cases is subgroup J has a probability score between 0.9 and 1.0, and none of those cases is metastasis free at the 5 year time point. Statistically significant differences are observed between the subgroups (p<0.0001), and 5-year MFS is shown in the figure legend.

Probability of the metastatic risk prediction is based upon the coefficients of the 28 variables (genes) and reported as a value between 0 and 1. For the two-class analysis, cases with a probability score between 0 and 0.5 are designated low risk, class 1 cases. Conversely, cases with a probability score between 0.5 and 1.0 are classified as class 2, high risk. The linear output of the probability score can also be used directly to assess the risk associated with the genetic signature of particular CM tumor. As shown in FIG. 7, 5 year MFS of cases in the 107 sample validation cohort is strongly correlated with the probability of metastasis. Assessment of all cases with a probability of metastasis lower than 0.399 shows that none of those cases has had a documented metastatic event to date, and 5 year MFS is 100%. Two of the 17 cases that fall between the probability scores of 0.4 and 0.499 have evidence of a metastatic event, and 5 year MFS for this group is 87%. Those cases with probability scores between 0.5 and 1.0 have a significant reduction in 5 year MFS. As illustrated by curves F-J in FIG. 5, 0.1 increment increases in the probability score lead to corresponding reductions in 5 year MFS from 56% to 46%, 22%, 16%, and 0%. Thus, the utility of the 28 gene predictive signature lies in both the class assignment of metastatic risk and the linear correlation of probability with metastatic outcome.

All references cited in this application are expressly incorporated by reference herein.

REFERENCES

1. Siegel R, Naishadham D, Jemal A. Cancer statistics, 2012. CA Cancer J Clin 2012; 62:10-29.
2. Balch C M, Soong S J, Gershenwald J E, et al. Prognostic factors analysis of 17,600 melanoma patients: validation of the American Joint Committee on Cancer melanoma staging system. J Clin Oncol 2001; 19:3622-34.
3. Balch C M, Gershenwald J E, Soong S J, et al. Final version of 2009 AJCC melanoma staging and classification. J Clin Oncol 2009; 27:6199-206.
4. Balch C M, Buzaid A C, Soong S J, et al. Final version of the American Joint Committee on Cancer staging system for cutaneous melanoma. J Clin Oncol 2001; 19:3635-48.
5. Edge S B, Compton C C. The American Joint Committee on Cancer: the 7th edition of the AJCC cancer staging manual and the future of TNM. Ann Surg Oncol 2010; 17:1471-4.
6. Takeuchi H, Morton D L, Kuo C, et al. Prognostic significance of molecular upstaging of paraffin-embedded sentinel lymph nodes in melanoma patients. J Clin Oncol 2004; 22:2671-80.
7. Zettersten E, Shaikh L, Ramirez R, Kashani-Sabet M. Prognostic factors in primary cutaneous melanoma. Surg Clin North Am 2003; 83:61-75.
8. Balch C M, Gershenwald J E, Soong S J, et al. Multivariate analysis of prognostic factors among 2,313 patients with stage III melanoma: comparison of nodal micrometastases versus macrometastases. J Clin Oncol 2010; 28:2452-9.
9. Yee V S, Thompson J F, McKinnon J G, et al. Outcome in 846 cutaneous melanoma patients from a single center after a negative sentinel node biopsy. Ann Surg Oncol 2005; 12:429-39.
10. Karim R Z, Scolyer R A, Li W, et al. False negative sentinel lymph node biopsies in melanoma may result from deficiencies in nuclear medicine, surgery, or pathology. Ann Surg 2008; 247:1003-10.
11. Nicholl M B, Elashoff D, Takeuchi H, Morton D L, Hoon D S. Molecular upstaging based on paraffin-embedded sentinel lymph nodes: ten-year follow-up confirms prognostic utility in melanoma patients. Ann Surg 2011; 253:116-22.
12. Coit D G. Melanoma Version 2.2013: National Comprehensive Cancer Network; 2013 2/2013.
13. Morton D L. Overview and update of the phase III Multicenter Selective Lymphadenectomy Trials (MSLT-I and MSLT-II) in melanoma. Clin Exp Metastasis 2012; 29:699-706.
14. Onken M D, Worley L A, Ehlers J P, Harbour J W. Gene expression profiling in uveal melanoma reveals two molecular classes and predicts metastatic death. Cancer Res 2004; 64:7205-9.
15. Francis P, Namlos H M, Muller C, et al. Diagnostic and prognostic gene expression signatures in 177 soft tissue sarcomas: hypoxia-induced transcription profile signifies metastatic potential. BMC Genomics 2007; 8:73.
16. Paik S, Shak S, Tang G, et al. A multigene assay to predict recurrence of tamoxifen-treated, node-negative breast cancer. N Engl J Med 2004; 351:2817-26.
17. Colman H, Zhang L, Sulman E P, et al. A multigene predictor of outcome in glioblastoma. Neuro Oncol 2010; 12:49-57.
18. Gordon G J, Jensen R V, Hsiao L L, et al. Using gene expression ratios to predict outcome among patients with mesothelioma. J Natl Cancer Inst 2003; 95:598-605.
19. Sato T. Locoregional management of hepatic metastasis from primary uveal melanoma. Semin Oncol 2010; 37:127-38.
20. Onken M D, Worley L A, Tuscan M D, Harbour J W. An accurate, clinically feasible multi-gene expression assay for predicting metastasis in uveal melanoma. J Mol Diagn 2010; 12:461-8.
21. Onken M D, Worley L A, Char D H, et al. Collaborative Ocular Oncology Group Report Number 1: Prospective Validation of a Multi-Gene Prognostic Assay in Uveal Melanoma. Ophthalmology 2012.
22. Jaeger J, Koczan D, Thiesen H J, et al. Gene expression signatures for tumor progression, tumor subtype, and tumor thickness in laser-microdissected melanoma tissues. Clin Cancer Res 2007; 13:806-15.
23. Bittner M, Meltzer P, Chen Y, et al. Molecular classification of cutaneous malignant melanoma by gene expression profiling. Nature 2000; 406:536-40.
24. Haqq C, Nosrati M, Sudilovsky D, et al. The gene expression signatures of melanoma progression. Proc Natl Acad Sci USA 2005; 102:6092-7.
25. Mauerer A, Roesch A, Hafner C, et al. Identification of new genes associated with melanoma. Exp Dermatol 2011; 20:502-7.
26. Scatolini M, Grand M M, Grosso E, et al. Altered molecular pathways in melanocytic lesions. Int J Cancer 2010; 126:1869-81.
27. Smith A P, Hoek K, Becker D. Whole-genome expression profiling of the melanoma progression pathway reveals marked molecular differences between nevi/melanoma in situ and advanced-stage melanomas. Cancer Biol Ther 2005; 4:1018-29.
28. Weeraratna A T, Becker D, Carr K M, et al. Generation and analysis of melanoma SAGE libraries: SAGE advice on the melanoma transcriptome. Oncogene 2004; 23:2264-74.
29. Winnepenninckx V, Lazar V, Michiels S, et al. Gene expression profiling of primary cutaneous melanoma and clinical outcome. J Natl Cancer Inst 2006; 98:472-82.

The invention claimed is:

1. A method of treating cutaneous melanoma in a patient having a primary cutaneous melanoma tumor, the method comprising:
    (a) determining a gene-expression profile signature for the patient having the primary cutaneous melanoma tumor by:
        (i) measuring gene expression levels of: KRT6B, GJA1, AQP3, TRIM29, TYRP1, RBM23, MGP, and EIF1B in a portion of the primary cutaneous melanoma tumor; and
        (ii) determining that the gene-expression profile signature indicates a class 2 (high risk) tumor having a probability value of between 0.500 and 1.00 when the expression level of: KRT6B is increased, GJA1 is decreased, AQP3 is decreased, TRIM29 is decreased, TYRP1 is decreased, RBM23 is decreased, MGP is decreased, and EIF1B is increased in the portion of the primary cutaneous melanoma tumor when compared to a non-metastatic sample;
    (b) administering a treatment to effectively treat cutaneous melanoma in the patient upon determining in step (a) that the gene-expression profile signature indicates a class 2 (high risk) tumor having a probability value of between 0.500 and 1.00 in order to increase relapse free survival of the patient.

2. The method of claim 1, wherein the portion of the primary cutaneous melanoma tumor is a sample selected from the group consisting of a formalin-fixed, paraffin embedded wide local excision sample and a formalin-fixed, paraffin embedded punch biopsy sample.

3. The method of claim 1, wherein the patient's sentinel lymph node is positive for metastatic cutaneous melanoma as determined by a sentinel lymph node biopsy.

4. The method of claim 1, wherein gene expression levels are measured using an assay selected from the group consisting of Polymerase Chain Reaction, Real-Time Polymerase Chain Reaction, direct DNA expression in microarray, Sanger sequencing analysis, Northern blot, direct RNA expression detection, serial analysis of gene expression, and next-generation RNA-sequencing.

5. The method of claim 4, wherein the assay is Real-Time Polymerase Chain Reaction.

6. The method of claim 1, wherein the treatment is selected from the group consisting of surgery and chemotherapy.

7. A method of treating cutaneous melanoma comprising administering a treatment to effectively treat cutaneous melanoma in a patient determined to have a primary cutaneous melanoma tumor with a probability value of between 0.500 and 1.00 when the expression level of KRT6B is increased, GJA1 is decreased, AQP3 is decreased, TRIM29 is decreased, TYRP1 is decreased, RBM23 is decreased, MGP is decreased, and EIF1B is increased in the portion of the primary cutaneous melanoma tumor when compared to a non-metastatic sample.

* * * * *